(12) United States Patent
Yabe et al.

(10) Patent No.: US 11,975,137 B2
(45) Date of Patent: May 7, 2024

(54) SYRINGE-SHAPED SPRAYING DEVICE

(71) Applicant: NIPRO CORPORATION, Osaka (JP)

(72) Inventors: Yukihiro Yabe, Osaka (JP); Kazuto Adachi, Osaka (JP)

(73) Assignee: NIPRO CORPORATION, Osaka (JP)

( * ) Notice: Subject to any disclaimer, the term of this patent is extended or adjusted under 35 U.S.C. 154(b) by 765 days.

(21) Appl. No.: 17/057,329

(22) PCT Filed: Apr. 16, 2019

(86) PCT No.: PCT/JP2019/016336
§ 371 (c)(1),
(2) Date: Nov. 20, 2020

(87) PCT Pub. No.: WO2019/225226
PCT Pub. Date: Nov. 28, 2019

(65) Prior Publication Data
US 2021/0196906 A1    Jul. 1, 2021

(30) Foreign Application Priority Data

May 24, 2018  (JP) ................................ 2018-099752

(51) Int. Cl.
*A61M 11/00*   (2006.01)
(52) U.S. Cl.
CPC ... *A61M 11/007* (2014.02); *A61M 2210/0618* (2013.01)
(58) Field of Classification Search
CPC .... A61M 5/345; A61M 11/007; A61M 5/348; A61M 15/08; F16J 15/3236
See application file for complete search history.

(56) References Cited

U.S. PATENT DOCUMENTS

| 2,811,155 | A | * | 10/1957 | Dunnican | ............... | A61M 5/34 |
| | | | | | | 604/242 |
| 3,491,757 | A | * | 1/1970 | Arce | ...................... | A61M 5/34 |
| | | | | | | 604/242 |

(Continued)

FOREIGN PATENT DOCUMENTS

| EP | 685237 A2 * 12/1995 | ............. A61M 5/28 |
| EP | 3 603 710 A1   2/2020 | |

(Continued)

OTHER PUBLICATIONS

Extended European Search Report dated Jan. 31, 2022 in European Application No. 19808229.9.

(Continued)

*Primary Examiner* — William R Carpenter
(74) *Attorney, Agent, or Firm* — Sughrue Mion, PLLC

(57) ABSTRACT

A syringe-shaped spraying device includes: a barrel; a nozzle; a packing disposed therebetween; and a core disposed inside the nozzle. The nozzle is connected to a connecting portion provided at a front end of the barrel. The nozzle has a first facing surface facing a front end surface of the connecting portion and a second facing surface facing an outer circumferential surface of the connecting portion. The outer circumferential surface is provided with an annular recess portion, and the second facing surface is provided with a first annular protrusion portion and a second annular protrusion portion. By engaging the first annular protrusion portion with the annular recess portion, the packing is compressed in an axial direction by the front end surface and the first facing surface. The second annular protrusion portion is in pressure contact with the outer circumferential surface of the connecting portion entirely in a circumferential direction.

2 Claims, 10 Drawing Sheets

(56) References Cited

U.S. PATENT DOCUMENTS

| | | | | |
|---|---|---|---|---|
| 5,154,325 A | * | 10/1992 | Ryder | B05B 11/047 |
| | | | | 222/215 |
| 5,601,077 A | * | 2/1997 | Imbert | A61M 15/0068 |
| | | | | 128/200.22 |
| 5,961,489 A | | 10/1999 | Hirota | |
| 10,335,556 B2 | * | 7/2019 | Vedrine | A61M 5/31531 |
| 2002/0174864 A1 | | 11/2002 | Alchas | |
| 2009/0143746 A1 | * | 6/2009 | Mudd | A61M 5/347 |
| | | | | 604/243 |
| 2012/0126035 A1 | | 5/2012 | Greiner-Perth et al. | |
| 2014/0303565 A1 | * | 10/2014 | Kubo | A61M 3/00 |
| | | | | 604/208 |
| 2015/0329271 A1 | | 11/2015 | Toma et al. | |
| 2016/0201830 A1 | * | 7/2016 | Le Quere | F16J 15/3236 |
| | | | | 285/349 |

FOREIGN PATENT DOCUMENTS

| | | |
|---|---|---|
| JP | 11-114065 A | 4/1994 |
| JP | 2001-137344 A | 5/2001 |
| JP | 2013-31599 A | 2/2013 |
| JP | 2014-513592 A | 6/2014 |
| JP | 2014-140588 A | 8/2014 |
| JP | 2014-140616 A | 8/2014 |
| JP | 2015-065985 A | 4/2015 |
| JP | 2015-123297 A | 7/2015 |
| JP | 2017-159096 A | 9/2017 |
| WO | WO-8603126 A * 6/1986 | ............. A61M 5/32 |
| WO | 2012/123532 A2 | 9/2012 |
| WO | 2012/123532 A3 | 9/2012 |
| WO | 2013/125555 A1 | 8/2013 |

OTHER PUBLICATIONS

Communication dated Nov. 22, 2022 from the Japanese Patent Office in JP Application No. 2018-99752.

International Search Report for PCT/JP2019/016336, dated Jun. 4, 2019.

* cited by examiner

SYRINGE-SHAPED SPRAYING DEVICE

CROSS REFERENCE TO RELATED APPLICATIONS

This application is a National Stage of International Application No. PCT/JP2019/016336 filed Apr. 16, 2019, claiming priority based on Japanese Patent Application No. 2018-099752 filed May 24, 2018.

TECHNICAL FIELD

The present invention relates to a syringe-shaped spraying device, particularly, to a syringe-shaped spraying device in which a core is disposed inside a nozzle attached to a front end of a barrel so as to define a liquid flow path by the nozzle and the core to increase pressure of a liquid to be discharged.

BACKGROUND ART

Unlike a general syringe, a syringe-shaped spraying device is an device that sprays a liquid in the form of a mist from a spraying hole by increasing, to a suitable level, pressure of the liquid to be discharged. In order to increase the pressure of the liquid to be discharged, it is effective to provide a liquid flow path with a sufficiently small cross sectional area. The liquid flow path includes the spraying hole.

For example, Japanese Patent Laying-Open No. 2001-137344 (PTL 1) discloses a syringe-shaped spraying device in which a cap-like nozzle is provided at a front end of a barrel of a syringe, a minute spraying hole is provided in the nozzle, and a valve is accommodated inside the nozzle. The valve has a function of providing a liquid flow path with a sufficiently small cross sectional area and preventing passage of a liquid insufficiently fed with pressure.

CITATION LIST

Patent Literature

PTL 1: Japanese Patent Laying-Open No. 2001-137344

SUMMARY OF INVENTION

Technical Problem

In general, in such a syringe-shaped spraying device, high pressure is generated inside the nozzle when discharging the liquid. Hence, the barrel and the nozzle need to be connected to each other liquid-tightly and firmly. If the connection between these portions is not sufficiently firm, not only liquid leakage occurs during use, but also the nozzle may fall from the barrel due to the pressure of the liquid.

Therefore, the present invention has been made in view of the above-described problem, and has an object to provide a syringe-shaped spraying device in which a nozzle is liquid-tightly and firmly connected to a front end of a barrel by way of a simple configuration.

Solution to Problem

A syringe-shaped spraying device according to the present invention includes a barrel, a plunger, a gasket, a nozzle, a packing, and a core. The barrel stores a liquid. The plunger has a front end inserted in the barrel, and the gasket is attached to the front end of the plunger. The nozzle is provided with a spraying hole for spraying the liquid, and is connected to a front end of the barrel. The packing has an annular shape and is interposed between the barrel and the nozzle. At least a portion of the core is disposed inside the nozzle, and a liquid flow path is defined between the core and the nozzle. A connecting portion that connects to the nozzle is provided at the front end of the barrel, the connecting portion having a tubular shape. The nozzle includes a first facing wall portion having an annular shape and a second facing wall portion having a tubular shape, the first facing wall portion having a first facing surface facing a front end surface of the connecting portion, the second facing wall portion having a second facing surface facing an outer circumferential surface of the connecting portion. The packing is disposed between the front end surface of the connecting portion and the first facing surface. The outer circumferential surface of the connecting portion is provided with an annular recess portion extending along a circumferential direction of the connecting portion, and the second facing surface is provided with a first annular protrusion portion, the first annular protrusion portion extending along a circumferential direction of the second facing wall portion, the first annular protrusion portion protruding inwardly in a radial direction of the second facing wall portion. By engaging the first annular protrusion portion with the annular recess portion, the packing is compressed in an axial direction due to the packing being sandwiched between the front end surface of the connecting portion and the first facing surface. The second facing surface is provided with a second annular protrusion portion at a portion located on a rear end side of the nozzle with respect to a portion of the second facing surface provided with the first annular protrusion portion, the second annular protrusion portion extending along the circumferential direction of the second facing wall portion, the second annular protrusion portion protruding inwardly in the radial direction of the second facing wall portion. The second annular protrusion portion is in pressure contact with the outer circumferential surface of the connecting portion entirely in the circumferential direction of the connecting portion.

In the syringe-shaped spraying device according to the present invention, a first lip portion having a protruding shape and extending along a circumferential direction of the packing may be provided at a first main surface of the packing, the first main surface having an annular shape, the first main surface facing the first facing surface. A second lip portion having a protruding shape and extending along the circumferential direction of the packing may be provided at a second main surface of the packing, the second main surface having an annular shape, the second main surface facing the front end surface of the connecting portion. In this case, each of the first lip portion and the second lip portion is preferably collapsed due to the packing being sandwiched between the front end surface of the connecting portion and the first facing surface.

In the syringe-shaped spraying device according to the present invention, the core may be inserted in and extend through the packing and may be inserted in the connecting portion.

Advantageous Effects of Invention

According to the present invention, there can be provided a syringe-shaped spraying device in which a nozzle is liquid-tightly and firmly connected to a front end of a barrel by way of a simple configuration.

DESCRIPTION OF EMBODIMENTS

Figure 1:
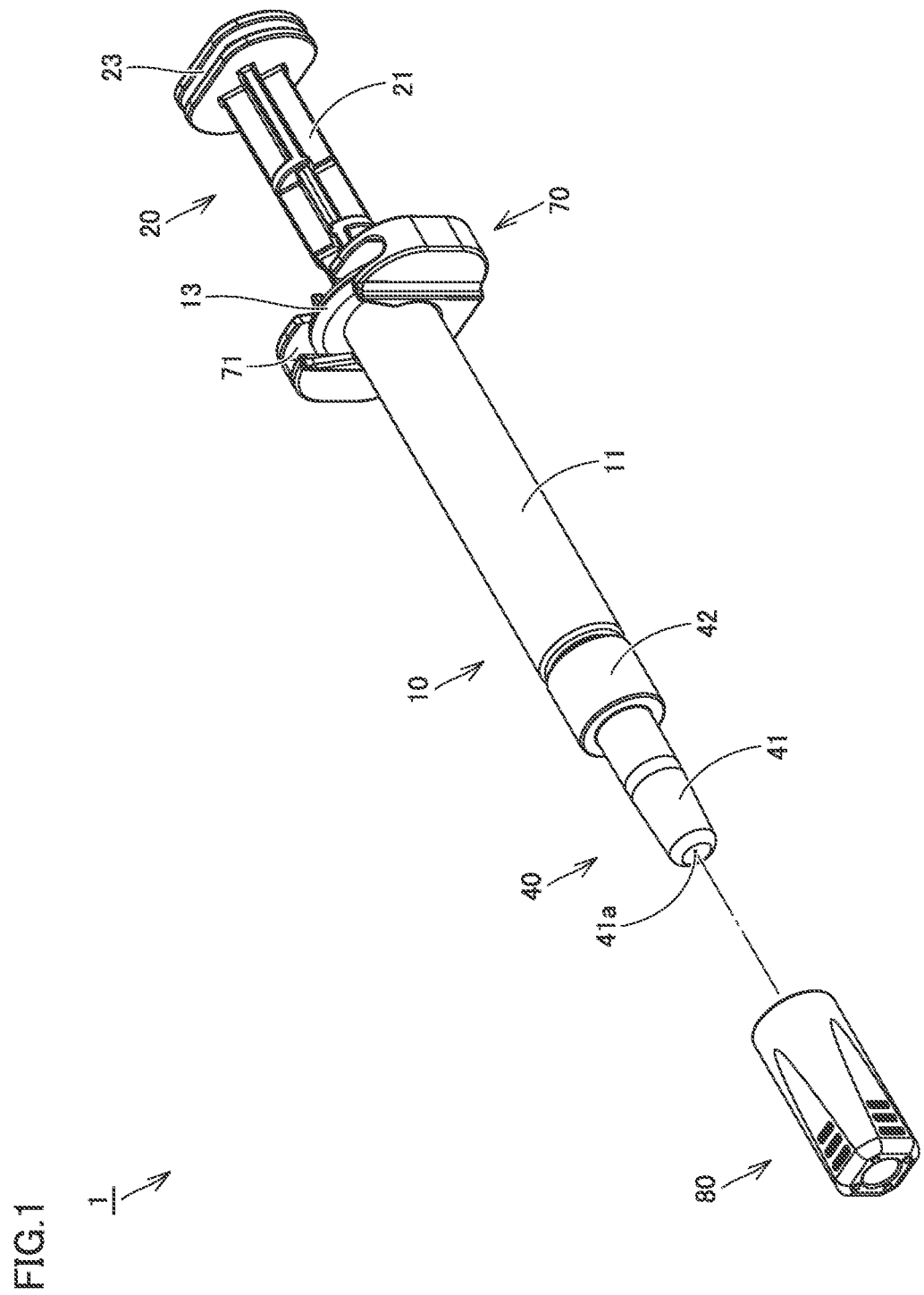
FIG. 1 is a perspective view of a syringe-shaped spraying device according to an embodiment.

Hereinafter, an embodiment of the present invention will be described in detail with reference to figures. The below-described embodiment illustrates a case where the present invention is applied to a pre-filled type syringe-shaped spraying device serving as a transnasal administration device for administering a liquid medicine to a pair of nasal cavities of a patient. It should be noted that in the below-described embodiment, the same or common portions are denoted by the same reference characters in the figures and will not be described repeatedly.

Figure 2:
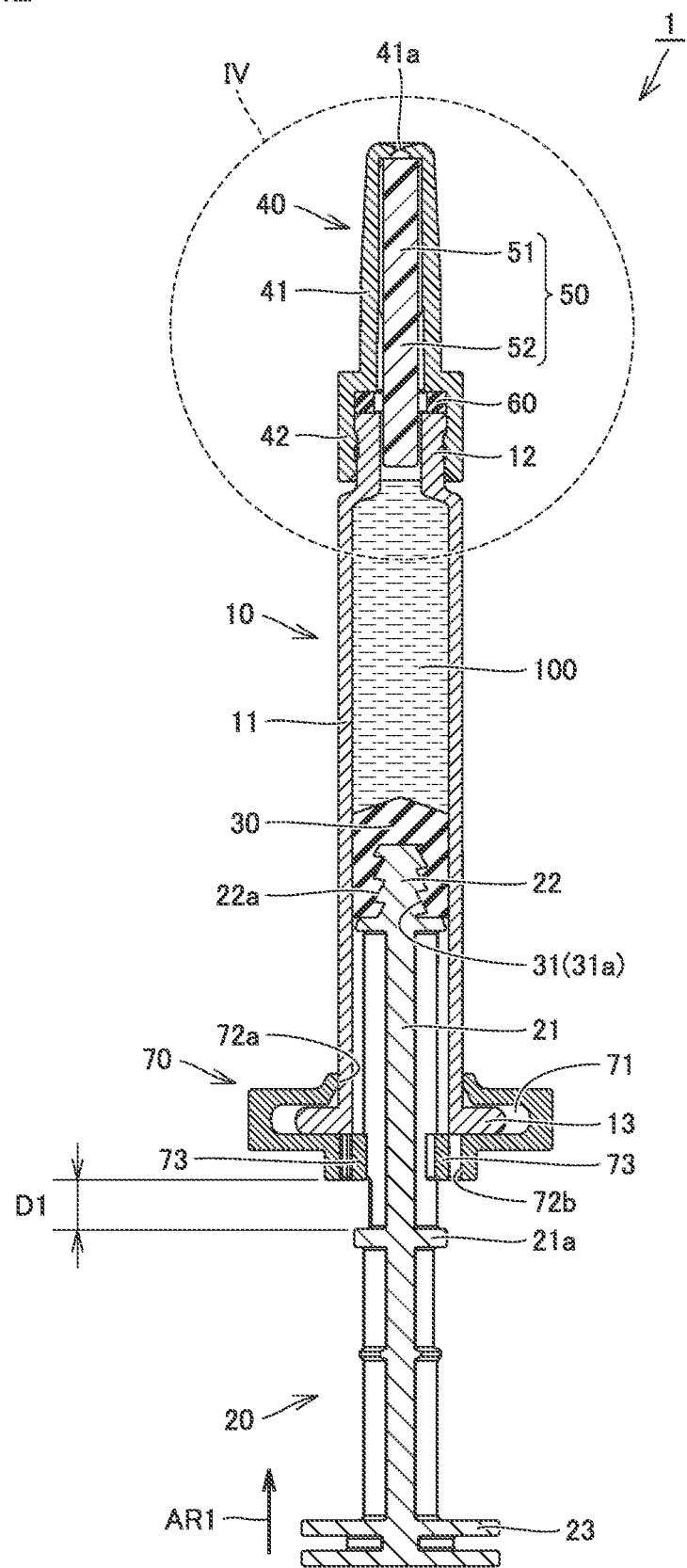
FIG. 2 is a cross sectional view of the syringe-shaped spraying device shown in FIG. 1.
Figure 3:
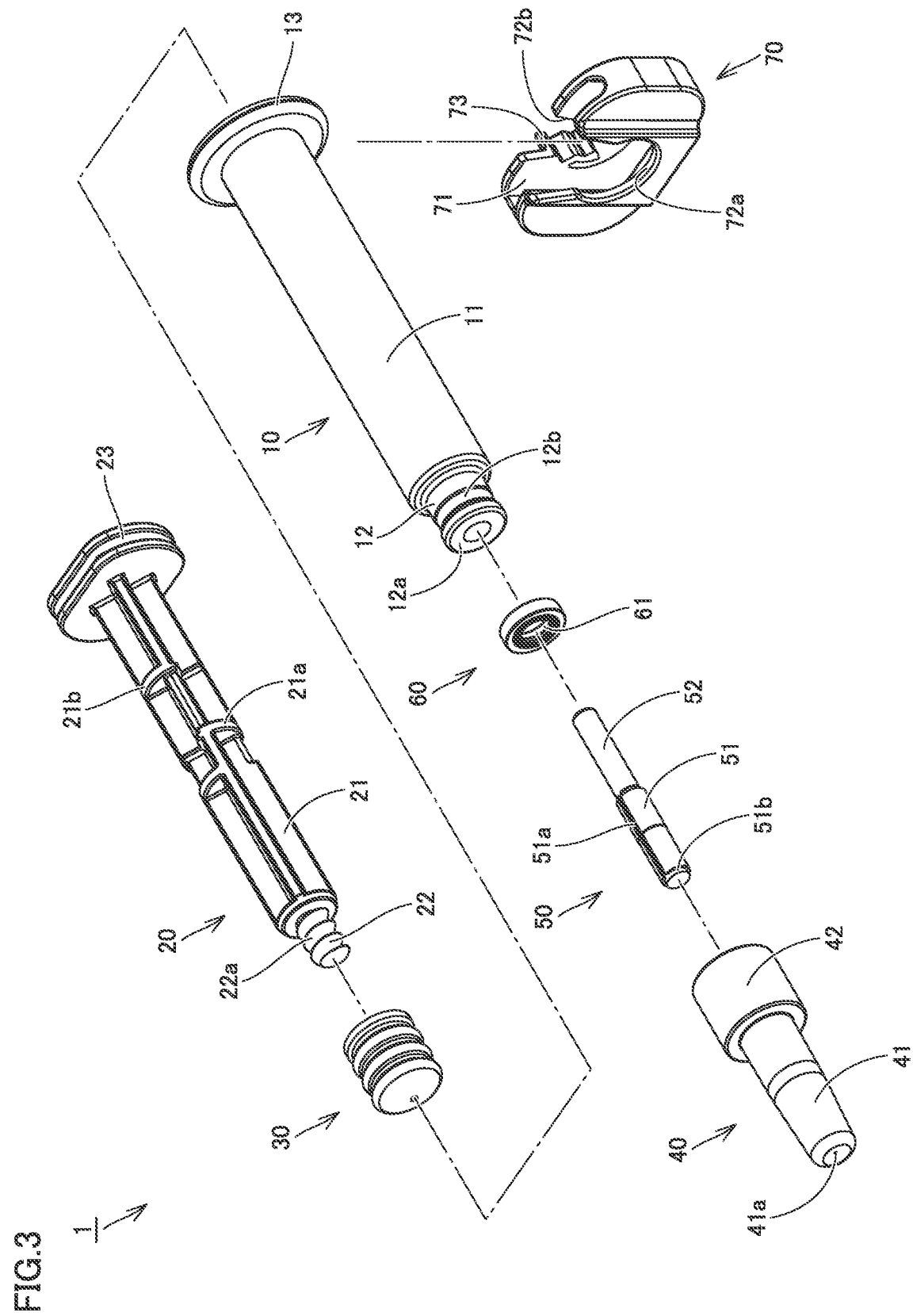
FIG. 3 is an exploded perspective view of the syringe-shaped spraying device shown in FIG. 1.

FIG. 1 is a perspective view of a syringe-shaped spraying device according to an embodiment of the present invention. FIG. 2 is a cross sectional view of the syringe-shaped spraying device shown in FIG. 1. FIG. 3 is an exploded perspective view thereof. First, referring to FIGS. 1 to 3, a schematic configuration of a syringe-shaped spraying device 1 according to the present embodiment will be described.

As shown in FIGS. 1 to 3, syringe-shaped spraying device 1 has an elongated bar-like shape as a whole, and mainly includes a barrel 10, a plunger 20, a gasket 30, a nozzle 40, a core 50, a packing 60, a finger grip 70, a cap 80, and a liquid medicine 100.

Barrel 10 is constituted of an elongated, substantially cylindrical member having open ends in the axial direction, and includes a tubular portion 11, a connecting portion 12, and a flange portion 13. Tubular portion 11 is constituted of a region having a cylindrical shape and extending along the axial direction. Connecting portion 12 is located at the front end of tubular portion 11, and is constituted of a decreased-diameter portion having a tubular shape and formed to have an outer diameter and an inner diameter smaller than those of tubular portion 11. Flange portion 13 is located at the rear end of tubular portion 11, and is constituted of an increased-diameter portion formed to have an outer diameter larger than that of tubular portion 11.

Barrel 10 has a hollow, cylindrical space therein, and gasket 30 is accommodated in the space. In the space formed inside barrel 10, liquid medicine 100 is provided on the front end side of barrel 10 with respect to the portion at which gasket 30 is located, and a front end of plunger 20 for pushing gasket 30 is inserted on the rear end side of barrel 10 with respect to the portion at which gasket 30 is located.

A material of barrel 10 is appropriately selected depending on a type of liquid medicine 100. Barrel 10 is desirably constituted of glass or constituted of an injection-molded product employing a resin material as a raw material. Barrel 10 is preferably transparent or translucent, and barrel 10 may be provided with a scale indicating a remaining amount of liquid medicine 100.

Plunger 20 is constituted of an elongated bar-like member, and includes a rod portion 21, a coupler portion 22, and a flange portion 23. Rod portion 21 is constituted of a region that extends along the axial direction and that has a cross section substantially in the form of a cross. Coupler portion 22 is provided to protrude from the front end of rod portion 21 along the axial direction of plunger 20, and has an outer circumferential surface provided with an external thread 22a. Flange portion 23 is constituted of a region that is substantially in the form of a plate and that includes a portion protruding from the rear end of rod portion 21 in a direction orthogonal to the axial direction of plunger 20.

The front end of plunger 20 is inserted from the rear end of barrel 10 to the inside of barrel 10. Plunger 20 is pushed by a user to move plunger 20 relative to barrel 10, with the result that gasket 30 is moved in barrel 10 to spray liquid medicine 100 from syringe-shaped spraying device 1.

Plunger 20 is desirably constituted of an injection-molded product employing a resin material as a raw material. It should be noted that first abutment portions 21a and second abutment portions 21b both protruding from the circumferential surface of rod portion 21 are provided at predetermined positions in the axial direction of plunger 20, and first abutment portions 21a and second abutment portions 21b will be described later.

Gasket 30 is constituted of a member having a substantially cylindrical shape, and is provided with an axial hole portion 31 at the rear end thereof in the axial direction. An internal thread 31a is provided in an inner circumferential surface of gasket 30. The inner circumferential surface defines axial hole portion 31.

Coupler portion 22 of plunger 20 is inserted in axial hole portion 31 of gasket 30. An external thread 22a provided in the outer circumferential surface of coupler portion 22 of plunger 20 is screwed into internal thread 31a provided in the inner circumferential surface of gasket 30 defining axial hole portion 31. Thus, gasket 30 is fixed to the front end of plunger 20 and is therefore attached to plunger 20.

Gasket 30 is accommodated in tubular portion 11 of barrel 10 in a slidable manner. More specifically, the outer circumferential surface of gasket 30 is in close contact with the inner circumferential surface of tubular portion 11 of barrel 10 such that the outer circumferential surface of gasket 30 is slidable on the inner circumferential surface of tubular portion 11 of barrel 10. Accordingly, liquid medicine 100 in barrel 10 is prevented from leaking to the plunger 20 side.

A material of gasket 30 is appropriately selected depending on a type of liquid medicine 100. Gasket 30 is desirably constituted of a rubber elastic body. Examples of the rubber elastic body usable herein include a butyl rubber, a butadiene rubber, an isoprene rubber, a silicone rubber, a thermoplastic elastomer, a silicone elastomer, and the like.

Nozzle 40 is constituted of a member having a substantially cylindrical shape with a bottom, and has a nozzle portion 41 and a connected portion 42. Nozzle portion 41 includes: a region having a substantially cylindrical shape and extending along the axial direction; and a bottom portion that closes the front end of the portion having the substantially cylindrical shape. A spraying hole 41a having a minute opening diameter is provided in the bottom portion. Connected portion 42 is located at the rear end of nozzle portion 41 and is constituted of an increased-diameter portion formed to have an outer diameter and an inner diameter larger than those of nozzle portion 41.

Nozzle 40 has a hollow, substantially cylindrical space therein, and connecting portion 12 of barrel 10, core 50 and packing 60 are accommodated in the space. Connecting portion 12 and packing 60 are located inside connected portion 42, and core 50 is located inside both nozzle portion 41 and connected portion 42.

Connecting portion 12 of barrel 10 is inserted into connected portion 42 of nozzle 40 from the rear end side of nozzle 40. Thus, nozzle 40 is connected to the front end of barrel 10. Specifically, since the inner diameter of connected portion 42 is slightly smaller than the outer diameter of connecting portion 12, nozzle 40 is connected to barrel 10 by press-fitting connecting portion 12 into connected portion 42. It should be noted that a more detailed connection structure between barrel 10 and nozzle 40 will be described later.

Nozzle 40 sprays liquid medicine 100 stored in barrel 10 to outside. Nozzle 40 has a flow path through which liquid medicine 100 flows during use. Nozzle 40 is provided with spraying hole 41a for spraying, to the outside, liquid medicine 100 having flown through the flow path.

Here, although details will be described later, the flow path for liquid medicine 100 inside nozzle 40 has a sufficiently small cross sectional area because core 50 is disposed inside nozzle 40. Accordingly, when plunger 20 is pushed into barrel 10 during use, the pressure of liquid medicine 100 is increased in the flow path, with the result that liquid medicine 100 is sprayed in the form of a mist from spraying hole 41a provided in nozzle 40.

A material of nozzle 40 is appropriately selected depending on a type of liquid medicine 100. Nozzle 40 is desirably constituted of an injection-molded product employing a resin material as a raw material.

Core 50 is constituted of a member having a substantially cylindrical shape, and has a large-diameter portion 51 located on the front end side and a small-diameter portion 52 located on the rear end side. The outer diameter of large-diameter portion 51 is substantially equal to the inner diameter of nozzle portion 41 of nozzle 40, and the outer diameter of small-diameter portion 52 is smaller than the inner diameter of nozzle portion 41 of nozzle 40.

First groove portions 51a extending along the axial direction are provided in the outer circumferential surface of large-diameter portion 51, and second groove portions 51b extending along the circumferential direction are provided in the front end of large-diameter portion 51. End portions of first groove portions 51a on the front end side of core 50 are connected to second groove portions 51b.

A material of core 50 is appropriately selected depending on a type of liquid medicine 100. Core 50 is desirably constituted of an injection-molded product employing a resin material as a raw material.

As described above, core 50 is accommodated inside nozzle 40 and the flow path for liquid medicine 100 is defined between core 50 and nozzle 40. Details thereof will be described later.

Packing 60 is constituted of an annular member provided with a through hole 61 extending therethrough in the axial direction, and is accommodated inside connected portion 42 of nozzle 40 as described above. Packing 60 is interposed between barrel 10 and nozzle 40, more specifically, is located between connecting portion 12 of barrel 10 and connected portion 42 of nozzle 40. Thus, packing 60 functions as a sealing member that prevents liquid medicine 100 from leaking from between barrel 10 and nozzle 40.

A material of packing 60 is appropriately selected depending on a type of liquid medicine 100. Packing 60 is desirably constituted of a rubber elastic body. Examples of the rubber elastic body usable herein include a butyl rubber, a butadiene rubber, an isoprene rubber, a silicone rubber, a thermoplastic elastomer, a silicone elastomer, and the like. Alternatively, packing 60 may be constituted of a resin member having an appropriate degree of elasticity instead of the rubber elastic body.

It should be noted that details of the connection structure, inclusive of packing 60, between barrel 10 and nozzle 40 will be described later.

Finger grip 70 has a flat box-like shape with an accommodation space 71 being formed therein and with a slit-like opening being provided at a side portion thereof. Finger grip 70 has a pair of wall portions located along the axial direction of barrel 10. Of the pair of wall portions, a wall portion located on the front end side is provided with a first insertion portion 72a in which tubular portion 11 of barrel 10 is inserted and through which tubular portion 11 of barrel 10 extends. Of the pair of wall portions, a wall portion located on the rear end side is provided with a second insertion portion 72b in which rod portion 21 of plunger 20 is inserted and through which rod portion 21 of plunger 20 extends.

Finger grip 70 is attached to flange portion 13 of barrel 10. More specifically, finger grip 70 is assembled to barrel 10 so as to accommodate flange portion 13 in accommodation space 71 through the slit-like opening provided at the side portion of finger grip 70.

Finger grip 70 is a region to be held by fingers of the user when pushing plunger 20 into barrel 10. It should be noted that finger grip 70 is constituted of, for example, an injection-molded product employing a resin material as a raw material.

Stoppers 73 each having a protruding shape are provided at second insertion portion 72b of finger grip 70. Stoppers 73 can be brought into abutment with first abutment portions 21a and second abutment portions 21b provided at rod portion 21 of plunger 20.

Here, first abutment portions 21a provided at plunger 20 are fan-shaped regions provided to connect a pair of adjacent wall portions of four wall portions located in the circumferential direction of rod portion 21 that is in the form of a cross when viewed in a cross section. In the present embodiment, a pair of first abutment portions 21a are provided at a pitch of 180° in the circumferential direction of rod portion 21.

Likewise, second abutment portions 21b provided at plunger 20 are fan-shaped portions provided to connect a pair of adjacent wall portions of the four wall portions located in the circumferential direction of rod portion 21 that is in the form of a cross when viewed in a cross section. In the present embodiment, a pair of second abutment portions 21b are provided at a pitch of 180° in the circumferential direction of rod portion 21.

The pair of second abutment portions 21b are provided at positions on the rear end side of plunger 20 with respect to the portions at which the pair of first abutment portions 21a are provided. The pair of second abutment portions 21b are provided at positions not overlapping with the pair of first abutment portions 21a in the axial direction of rod portion 21.

On the other hand, stoppers 73 provided at finger grip 70 protrude inwardly from an edge portion of second insertion portion 72b. A pair of stoppers 73 are provided at a pitch of 180° along the circumferential direction of second insertion portion 72b.

Thus, in a state in which the pair of first abutment portions 21a and the pair of stoppers 73 overlap with each other in the axial direction of plunger 20, the pair of first abutment portions 21a and the pair of stoppers 73 are brought into abutment with each other when plunger 20 is pushed, with the result that the pushing of plunger 20 is stopped. On the other hand, in a state in which the pair of first abutment portions 21a and the pair of stoppers 73 do not overlap with each other in the axial direction of plunger 20, the pair of first abutment portions 21a and the pair of stoppers 73 are not brought into abutment with each other when plunger 20 is pushed, with the result that the pushing of plunger 20 is not stopped.

Likewise, in a state in which the pair of second abutment portions 21b and the pair of stoppers 73 overlap with each other in the axial direction of plunger 20, the pair of second abutment portions 21b and the pair of stoppers 73 are brought into abutment with each other when plunger 20 is pushed, with the result that the pushing of plunger 20 is stopped. On the other hand, in a state in which the pair of second abutment portions 21b and the pair of stoppers 73 do not overlap with each other in the axial direction of plunger 20, the pair of second abutment portions 21b and the pair of stoppers 73 are not brought into abutment with each other when plunger 20 is pushed, with the result that the pushing of plunger 20 is not stopped.

Therefore, by rotating plunger 20 in the circumferential direction with respect to the axis of plunger 20 with the front end of plunger 20 being inserted in barrel 10, movement of plunger 20 becomes restricted or unrestricted by finger grip 70. Hence, by appropriately adjusting the positions of first abutment portions 21a and second abutment portions 21b provided at plunger 20, an amount of liquid medicine 100 to be administered by one pushing operation on plunger 20 can be adjusted to a predetermined amount.

Cap 80 has a substantially polygonal tubular shape with a bottom, and is detachably attached to nozzle 40. Cap 80 is attached to nozzle 40 so as to cover nozzle portion 41 of nozzle 40 when syringe-shaped spraying device 1 is not in use. Thus, when syringe-shaped spraying device 1 is not in use, the vicinity of spraying hole 41a provided in nozzle 40 is kept clean by cap 80.

A material of cap 80 is appropriately selected depending on a type of liquid medicine 100. Cap 80 is desirably constituted of a rubber elastic body. Examples of the rubber elastic body usable herein include a butyl rubber, a butadiene rubber, an isoprene rubber, a silicone rubber, a thermoplastic elastomer, a silicone elastomer, and the like. Further, cap 80 may be constituted of a resin member having an appropriate degree of elasticity instead of the rubber elastic body.

Figure 4:
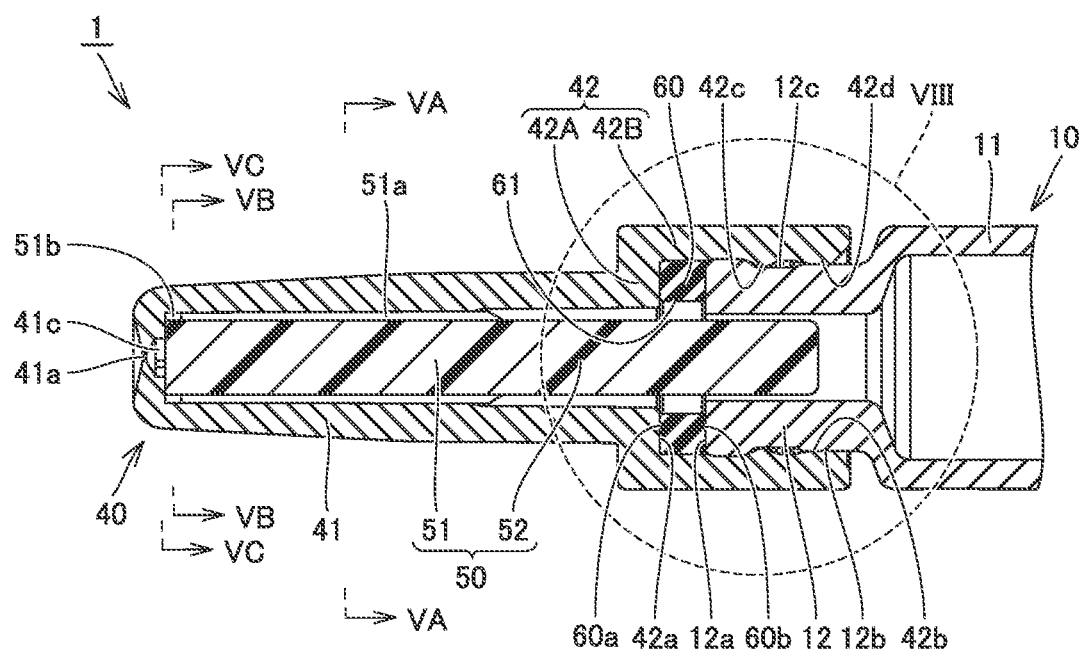
FIG. 4 is an enlarged view of a region IV shown in FIG. 2.
Figure 5C:
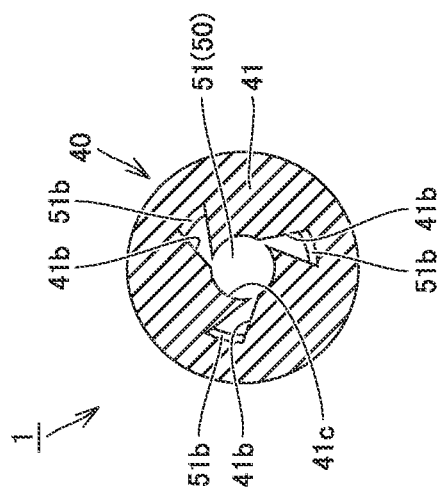
FIGS. 5(A) to 5(C) are cross sectional views taken along each of lines VA-VA, VB-VB, and VC-VC shown in FIG. 4.
Figure 5B:
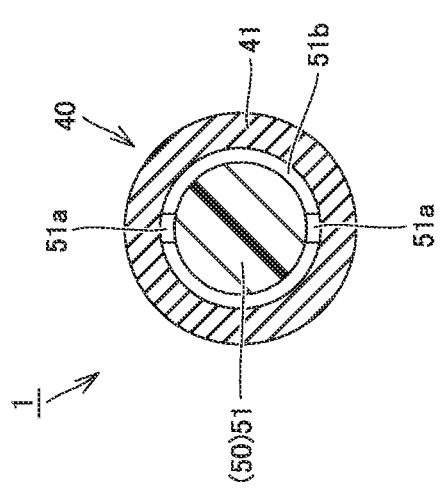
Figure 5A:
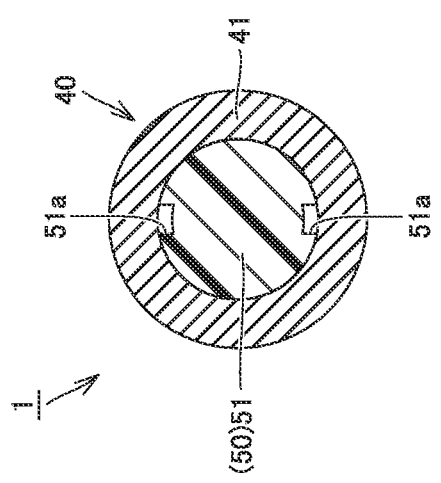

FIG. 4 is an enlarged view of a region IV shown in FIG. 2. FIGS. 5(A) to 5(C) are cross sectional views taken along lines VA-VA, VB-VB, and VC-VC shown in FIG. 4, respectively. Referring to FIGS. 4 and 5(A) to 5(C), the following fully describes a configuration of the flow path for liquid medicine 100 inside nozzle 40 of syringe-shaped spraying device 1 according to the present embodiment. It should be noted that in each of FIGS. 4 and 5, liquid medicine 100 is not shown for ease of understanding.

As shown in FIG. 4, by providing through hole 61 in packing 60 interposed between barrel 10 and nozzle 40, the space inside barrel 10 and the space inside nozzle 40 communicate with each other via through hole 61. On the other hand, small-diameter portion 52 located at the rear end side of core 50 is inserted in and extends through packing 60 and is inserted in connecting portion 12 of barrel 10.

Here, the inner diameter of packing 60 and the inner diameter of connecting portion 12 are both larger than the outer diameter of small-diameter portion 52 of core 50. Thus, a minute clearance is formed between small-diameter portion 52 of core 50 and each of packing 60 and connecting portion 12, with the result that a flow path for liquid medicine 100 with a sufficiently small cross sectional area is defined by the clearance.

In the space inside nozzle 40, small-diameter portion 52 of core 50 is located within a space located on the rear end side of nozzle portion 41, i.e., at the portion adjacent to through hole 61 of packing 60. As described above, the outer diameter of small-diameter portion 52 is smaller than the inner diameter of nozzle portion 41. Thus, a minute clearance is also formed between small-diameter portion 52 of core 50 and nozzle portion 41, with the result that a flow path for liquid medicine 100 with a sufficiently small cross sectional area is defined by the clearance.

As shown in FIGS. 4, 5(A), and 5(B), in the space inside nozzle 40, a flow path for liquid medicine 100 is defined within a space within which large-diameter portion 51 of core 50 is disposed, mainly by first groove portions 51a provided in the outer circumferential surface of large-diameter portion 51 and second groove portions 51b provided in the front end of large-diameter portion 51.

More specifically, since the outer diameter of large-diameter portion 51 is substantially equal to the inner diameter of nozzle portion 41 as described above, a flow path for liquid medicine 100 with a sufficiently small cross sectional area is defined by surfaces of first groove portions 51a and surfaces of second groove portions 51b as well as portions of the inner circumferential surface of nozzle portion 41 facing the surfaces of first groove portions 51a and the surfaces of second groove portions 51b. It should be noted that in the present embodiment, a pair of first groove portions 51a are provided at a pitch of 180° in the circumferential direction of core 50.

On the other hand, as shown in FIGS. 4 and 5(C), a plurality of first flow path portions 41b radially extending to communicate with second groove portions 51b are provided at the front end (i.e., the bottom portion of nozzle portion 41) of nozzle 40 in which spraying hole 41a is provided. A second flow path portion 41c defined by a cylindrical space is provided in the bottom portion of a portion of nozzle portion 41 corresponding to the central portion of the plurality of first flow path portions 41b extending radially. Each of the plurality of first flow path portions 41b communicates with second flow path portion 41c. Second flow path portion 41c also communicates with spraying hole 41a.

Here, each of the plurality of first flow path portions 41b and second flow path portion 41c is formed to be sufficiently minute. Thus, a flow path for liquid medicine 100 with a sufficiently small cross sectional area is defined by the plurality of first flow path portions 41b and second flow path portion 41c.

As described above, in syringe-shaped spraying device 1 according to the present embodiment, since core 50 is accommodated inside nozzle 40, the cross sectional area of the flow path for liquid medicine 100 defined by nozzle 40 and core 50 is sufficiently small. Hence, the pressure of liquid medicine 100 in the flow path is increased, with the result that liquid medicine 100 is sprayed in the form of a mist from spraying hole 41a.

Figure 6A:
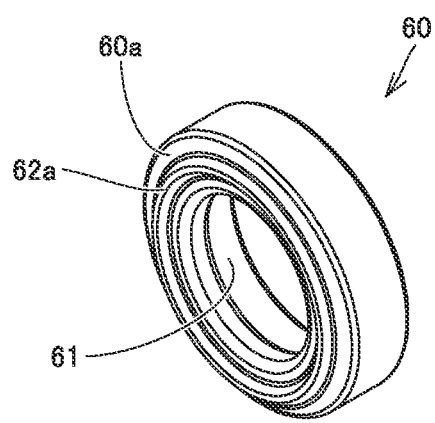
FIGS. 6(A) and 6(B) are perspective views of a packing shown in FIG. 2.
Figure 6B:
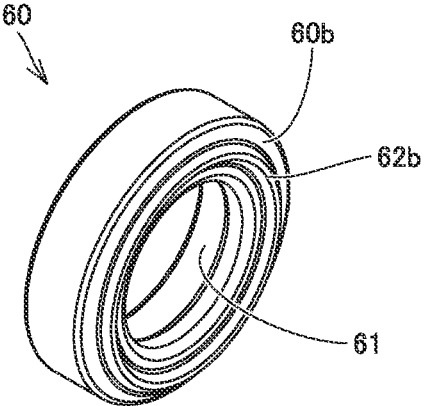
Figure 7:
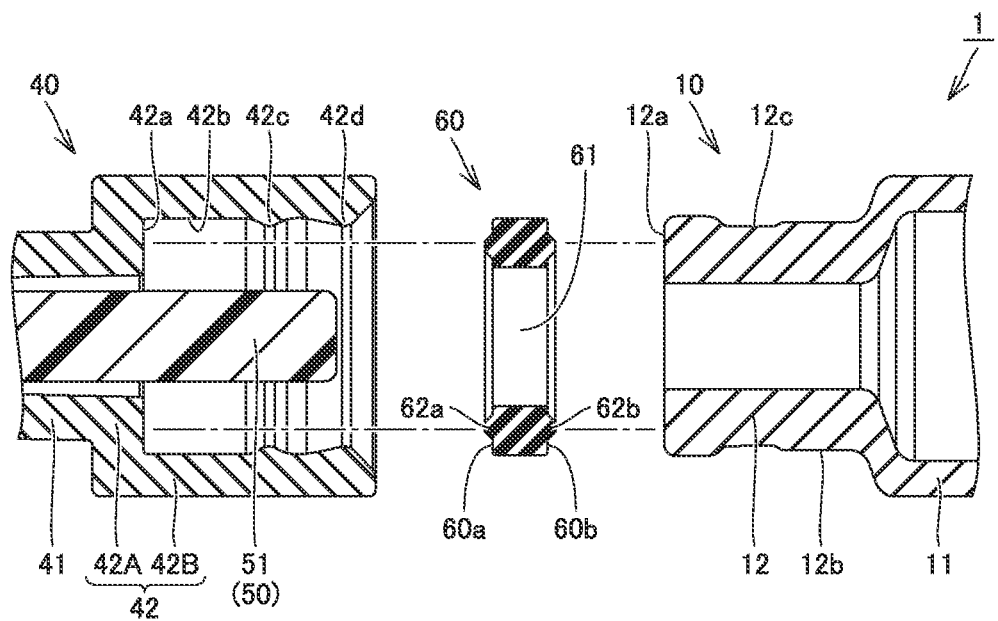
FIG. 7 is an exploded view showing a structure in which the packing shown in FIG. 2 is assembled.
Figure 8:
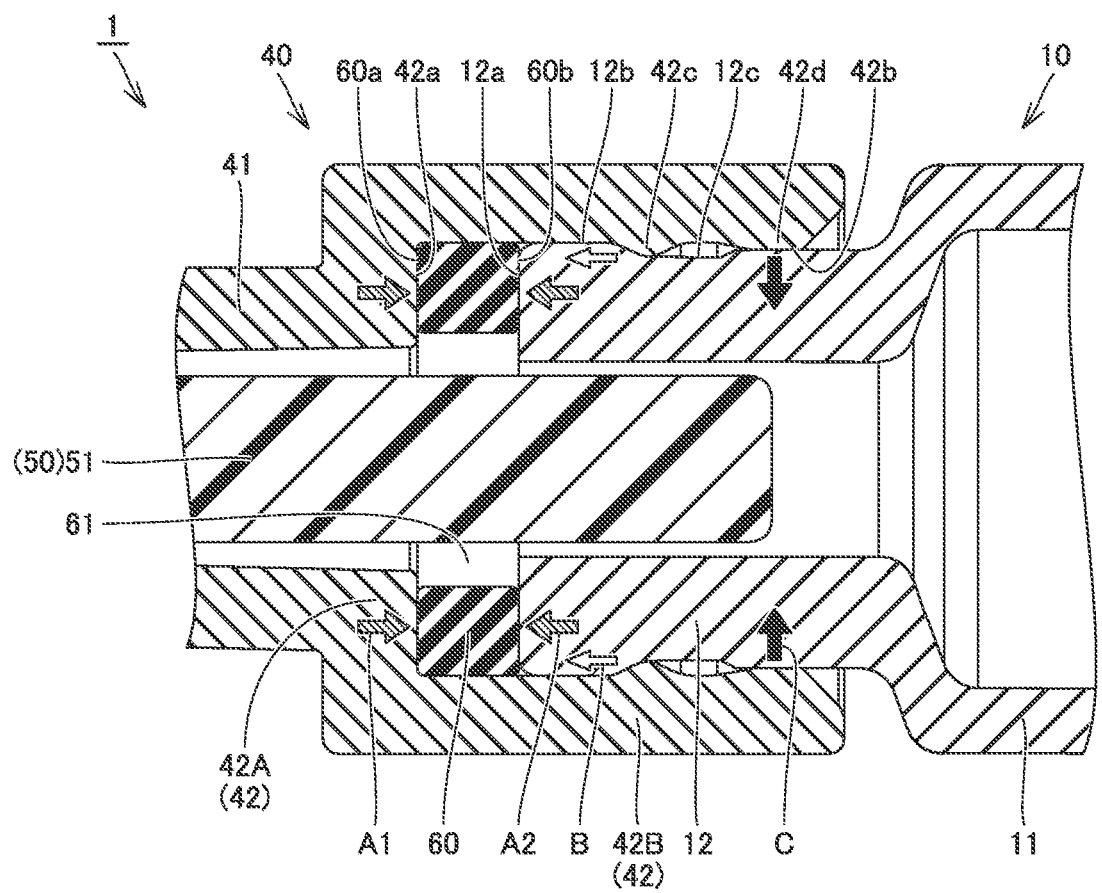
FIG. 8 is an enlarged view of a region VIII shown in FIG. 4.

Each of FIGS. 6(A) and 6(B) is a perspective view of the packing shown in FIG. 2. FIG. 7 is an exploded view showing a structure in which the packing is assembled. FIG. 8 is an enlarged view of a region VIII shown in FIG. 4. Referring to FIGS. 6(A) to 8 as well as FIGS. 3 and 4, the following describes a structure in which nozzle 40 is assembled to barrel 10 in syringe-shaped spraying device 1 according to the present embodiment.

As shown in FIGS. 6(A), 6(B), and 7, packing 60, which has an annular shape and is provided with through hole 61, has a first main surface 60a and a second main surface 60b. First main surface 60a and second main surface 60b are a pair of main surfaces located in the axial direction. Each of first main surface 60a and second main surface 60b has an annular shape to surround through hole 61. First main surface 60a is provided with a first lip portion 62a having a protruding shape and extending along the circumferential direction. Second main surface 60b is provided with a second lip portion 62b extending along the circumferential direction.

As shown in FIG. 7, by sandwiching packing 60 between nozzle 40 and barrel 10 with first main surface 60a being disposed on the nozzle 40 side and second main surface 60b being disposed on the barrel 10 side, packing 60 is assembled to syringe-shaped spraying device 1. More specifically, packing 60 is assembled to barrel 10 and nozzle 40 with packing 60 being compressed by barrel 10 and nozzle 40 in the axial direction.

Here, as shown in FIGS. 3, 4, 7 and 8, connecting portion 12 of barrel 10 has a front end surface 12a having an annular shape and an outer circumferential surface 12b constituted of a substantially cylindrical surface. An annular recess portion 12c extending along the circumferential direction is provided at a predetermined position of outer circumferential surface 12b.

On the other hand, connected portion 42 of nozzle 40 has: a first facing wall portion 42A having an annular plate-like shape and located at the rear end of nozzle portion 41; and a second facing wall portion 42B having a substantially cylindrical shape and extending continuously from the outer edge of first facing wall portion 42A. First facing wall portion 42A has a first facing surface 42a facing front end surface 12a of connecting portion 12 of barrel 10, and second facing wall portion 42B has a second facing surface 42b facing outer circumferential surface 12b of connecting portion 12 of barrel 10.

First facing surface 42a has an annular shape, and second facing surface 42b is constituted of a substantially cylindrical surface. A first annular protrusion portion 42c extending along the circumferential direction and protruding inwardly in the radial direction is provided at a predetermined position of second facing surface 42b. A second annular protrusion portion 42d extending along the circumferential direction and protruding inwardly in the radial direction is provided at a portion of second facing surface 42b located on the rear end side of nozzle 40 with respect to the portion at which first annular protrusion portion 42c is provided.

As shown in FIG. 7, nozzle 40 is connected to barrel 10 by press-fitting connecting portion 12 of barrel 10 into connected portion 42 of nozzle 40. On this occasion, by interposing packing 60 between first facing surface 42a of nozzle 40 and front end surface 12a of barrel 10, packing 60 is sandwiched between first facing surface 42a and front end surface 12a.

As shown in FIG. 8, in the state after the assembly, first annular protrusion portion 42c provided at second facing surface 42b of connected portion 42 of nozzle 40 is engaged with annular recess portion 12c provided at outer circumferential surface 12b of connecting portion 12 of barrel 10. Accordingly, barrel 10 and nozzle 40 are restricted from being moved in directions in which they are separated further away from each other.

On this occasion, first main surface 60a of packing 60 is disposed on the nozzle 40 side, and second main surface 60b of packing 60 is disposed on the barrel 10 side. Therefore, after the assembly, first main surface 60a of packing 60 is in abutment with first facing surface 42a of nozzle 40, and second main surface 60b of packing 60 is in abutment with front end surface 12a of barrel 10.

Accordingly, packing 60 receives forces from first facing surface 42a of nozzle 40 and front end surface 12a of barrel 10 in opposite directions, i.e., directions of arrows A1 and A2 shown in the figure, with the result that packing 60 is compressed in the axial direction.

On the other hand, in response to a restoring force of compressed packing 60, annular recess portion 12c of barrel 10 receives a force from first annular protrusion portion 42c of nozzle 40 in a direction of arrow B shown in the figure (i.e., toward the packing 60 side).

Accordingly, nozzle 40 and barrel 10 are fixed in the axial direction, thereby connecting nozzle 40 to barrel 10.

It should be noted that on this occasion, each of first lip portion 62a and second lip portion 62b provided at packing 60 is compressed due to packing 60 being sandwiched between first facing surface 42a of nozzle 40 and front end surface 12a of barrel 10. Thus, first main surface 60a of packing 60 and first facing surface 42a of nozzle 40 are brought into close contact with each other, and second main surface 60b of packing 60 and front end surface 12a of barrel 10 are brought into close contact with each other, with the result that the space inside nozzle 40 is sealed from outside at these portions in a liquid-tight manner.

Here, in the case where nozzle 40 is fixed to barrel 10 only by engagement between annular recess portion 12c and first annular protrusion portion 42c, nozzle 40 and barrel 10 are fixed only in the axial direction as described above. Hence, when an external force is applied in a direction intersecting the axial direction, great looseness may occur between barrel 10 and nozzle 40.

Liquid medicine 100 may be leaked from between barrel 10 and nozzle 40 due to occurrence of such looseness during use as well as the increased pressure of liquid medicine 100 inside nozzle 40, particularly. Further, when such looseness occurs during use, nozzle 40 is axially displaced with respect to barrel 10 to cause displacement in the spraying direction of liquid medicine 100, with the result that liquid medicine 100 may be hindered from being administered to a target position.

To address this, in syringe-shaped spraying device 1 according to the present embodiment, second annular protrusion portion 42d extending along the circumferential direction and protruding inwardly in the radial direction is provided at the portion of second facing surface 42b located on the rear end side of nozzle 40 with respect to the portion at which first annular protrusion portion 42c is provided as described above, thereby suppressing the occurrence of looseness.

That is, as shown in FIG. 8, by providing second annular protrusion portion 42d at second facing surface 42b in pressure contact with outer circumferential surface 12b of connecting portion 12 entirely in the circumferential direction of connecting portion 12 of barrel 10, connecting portion 12 receives a force from second annular protrusion portion 42d of connected portion 42 in a direction of arrow C shown in the figure (i.e., inwardly in the radial direction). At this portion, nozzle 40 and barrel 10 are fixed in the radial direction.

Therefore, by employing this configuration, nozzle 40 and barrel 10 are fixed not only in the axial direction but also in the radial direction, with the result that nozzle 40 is connected to barrel 10 liquid-tightly and firmly. Therefore, even when an external force is applied to nozzle 40 or barrel 10 in a direction intersecting the axial direction, no great looseness occurs between barrel 10 and nozzle 40, with the result that occurrence of liquid leakage can be significantly suppressed.

This effect can be obtained not only in a non-used state but also in a used state in which the pressure of liquid medicine 100 is increased inside nozzle 40. That is, by employing the above-described configuration, nozzle 40 is connected to barrel 10 liquid-tightly and firmly, with the result that occurrence of liquid leakage can be suppressed even when the above-described external force is applied during use of syringe-shaped spraying device 1.

Further, according to syringe-shaped spraying device 1, looseness between barrel 10 and nozzle 40 can be suppressed as described above. Hence, nozzle 40 can be prevented in advance from being axially displaced with respect to barrel 10, thus avoiding displacement of the spraying direction of liquid medicine 100. Accordingly, liquid medicine 100 can be administered to a target position, advantageously.

Further, according to syringe-shaped spraying device 1, nozzle 40 can be liquid-tightly and firmly connected to barrel 10 by way of the very simple configuration in which second annular protrusion portion 42d is provided at second facing surface 42b of connected portion 42 of nozzle 40. Hence, syringe-shaped spraying device 1 with high performance can be provided at low cost without increasing manufacturing cost.

Figure 9:
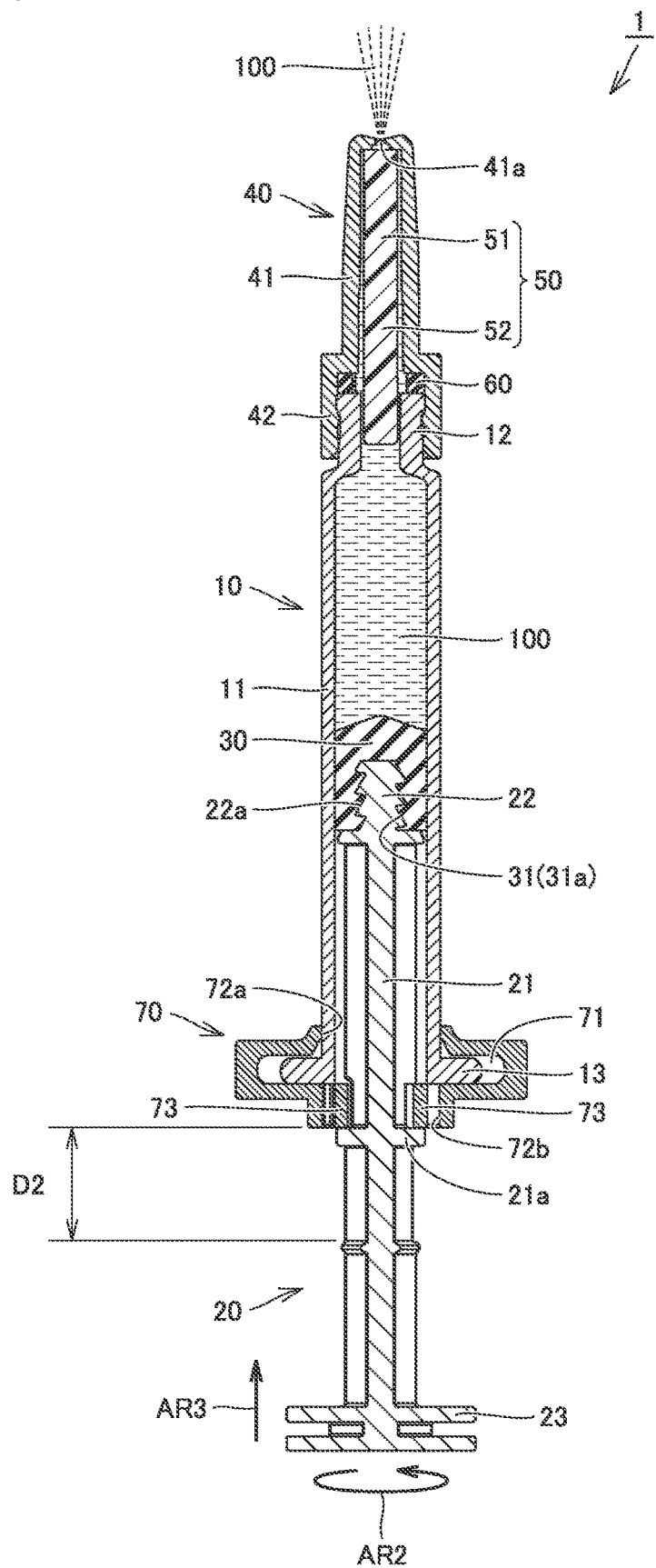
FIG. 9 is a cross sectional view showing a state at the time of completion of a first stage during use of the syringe-shaped spraying device shown in FIG. 1.
Figure 10:
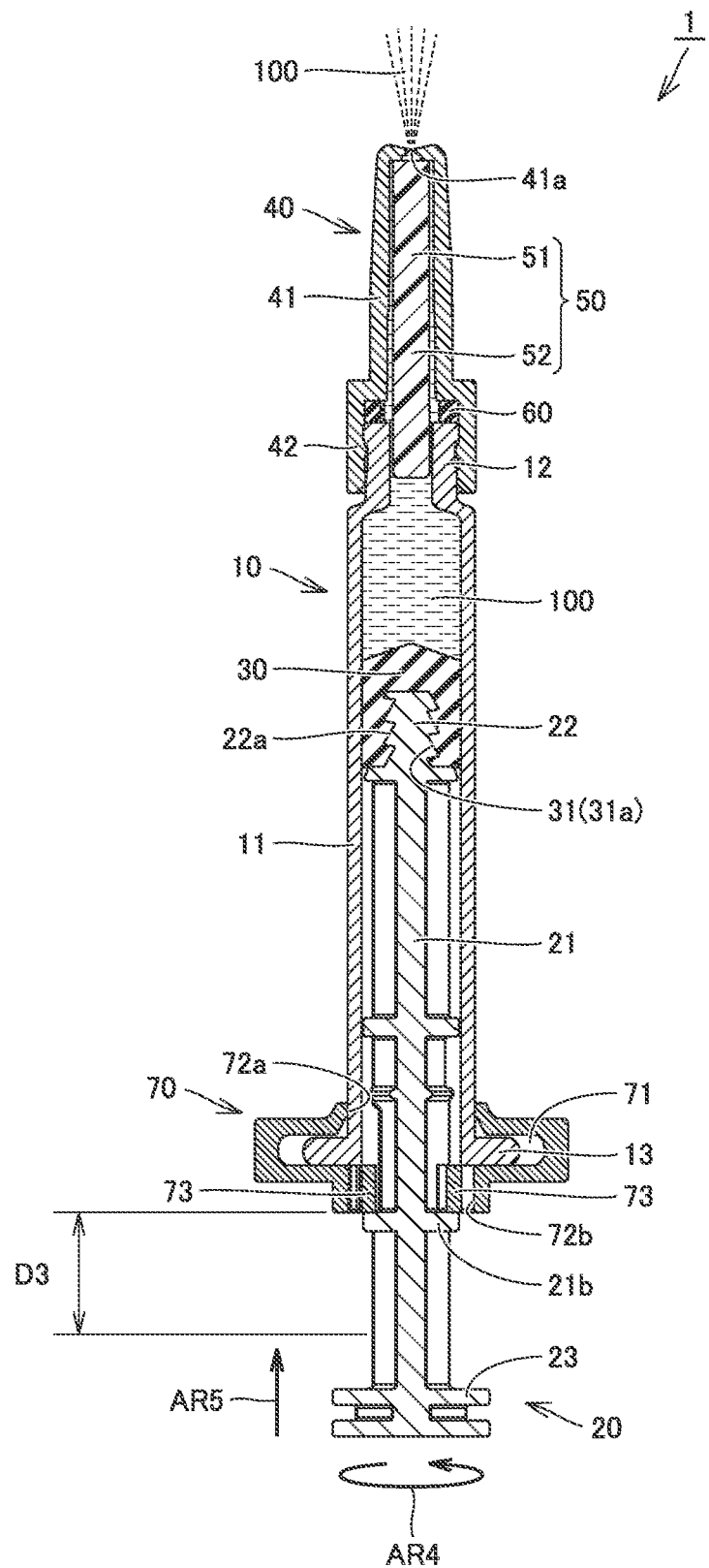
FIG. 10 is a cross sectional view showing a state at the time of completion of a second stage during use of the syringe-shaped spraying device shown in FIG. 1.
Figure 11:
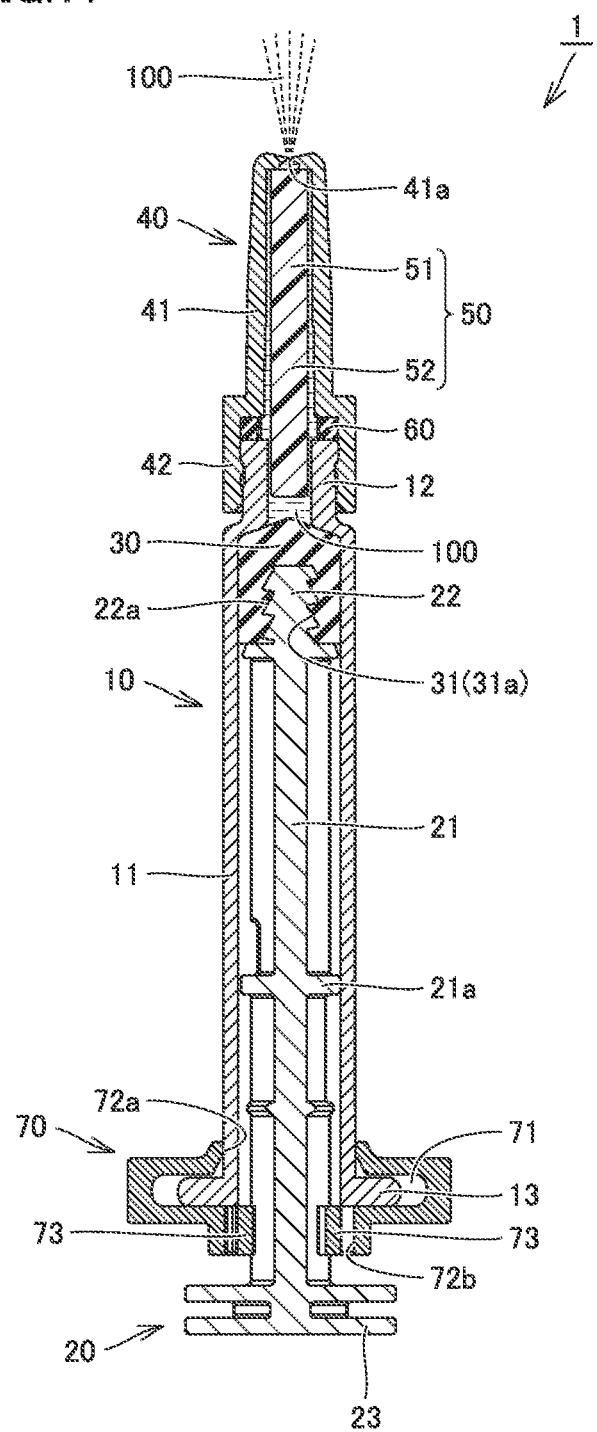
FIG. 11 is a cross sectional view showing a state at the time of completion of a third stage during use of the syringe-shaped spraying device shown in FIG. 1.

FIGS. 9 to 11 are cross sectional views showing respective states of the syringe-shaped spraying device shown in FIG. 1 at the times of completion of first to third stages during use of the syringe-shaped spraying device. Referring to FIGS. 9 to 11 as well as FIG. 2, the following describes a manner of use of syringe-shaped spraying device 1 according to the present embodiment.

As shown in FIG. 2, in order to use syringe-shaped spraying device 1, first, syringe-shaped spraying device 1 is brought into a standing posture such that nozzle 40 is located at the upper side in the vertical direction and plunger 20 is located at the lower side in the vertical direction. In this state, cap 80 is removed.

Next, as shown in FIG. 2, as the first stage, the user operates plunger 20 and pushes plunger 20 in a direction of arrow AR1 (i.e., toward the barrel 10 side) shown in the figure. On this occasion, the pair of first abutment portions 21a provided at rod portion 21 of plunger 20 are brought into abutment with the pair of stoppers 73 provided at finger grip 70, with the result that plunger 20 is stopped at the time when plunger 20 is moved by a distance D1 shown in the figure.

In the first stage, as shown in FIG. 9, due to the movement of plunger 20 by distance D1, air inside barrel 10 and nozzle 40 and an excess of liquid medicine 100 in barrel 10 (i.e., an amount obtained by subtracting, from the total amount of liquid medicine 100 in barrel 10, an amount of liquid medicine 100 to be administered to one nasal cavity, an amount of liquid medicine 100 to be administered to the other nasal cavity, and an amount of liquid medicine 100 to remain inside barrel 10 and nozzle 40 after completion of the administration) are sprayed from spraying hole 41a to the outside of syringe-shaped spraying device 1. Accordingly, barrel 10 and nozzle 40 are entirely filled with liquid medicine 100, thus completing preparation for administration of liquid medicine 100.

Next, as shown in FIG. 9, as the second stage, the user operates plunger 20 and rotates plunger 20 in a direction of arrow AR2 shown in the figure, with the result that the pair of first abutment portions 21a and the pair of stoppers 73 are brought out of abutment. Thereafter, the user inserts the front end of nozzle 40 into one nasal cavity, operates plunger 20, and pushes plunger 20 in a direction of arrow AR3 shown in the figure (i.e., toward the barrel 10 side). On this occasion, the pair of second abutment portions 21b provided at rod portion 21 of plunger 20 are brought into abutment with the pair of stoppers 73 provided at finger grip 70, with the result that plunger 20 is stopped at the time when plunger 20 is moved by a distance D2 shown in the figure.

In the second stage, as shown in FIG. 10, due to the movement of plunger 20 by distance D2, an amount of liquid medicine 100 corresponding to the predetermined amount of liquid medicine 100 to be administered to one nasal cavity is sprayed from spraying hole 41a to the outside of syringe-shaped spraying device 1. In this way, the administration of liquid medicine 100 to one nasal cavity is completed.

Next, as shown in FIG. 10, as the third stage, the user operates plunger 20 and rotates plunger 20 in a direction of arrow AR4 shown in the figure, with the result that the pair of second abutment portions 21b and the pair of stoppers 73 are brought out of abutment. Thereafter, the user inserts the front end of nozzle 40 into the other nasal cavity, operates plunger 20, and pushes plunger 20 in a direction of arrow AR5 shown in the figure (i.e., toward the barrel 10 side). On this occasion, the front end of gasket 30 is brought into abutment with an end portion of tubular portion 11 on the connecting portion 12 side of barrel 10, with the result that plunger 20 is stopped at the time when plunger 20 is moved by a distance D3 shown in the figure.

In the third stage, as shown in FIG. 11, due to the movement of plunger 20 by distance D3, an amount of liquid medicine 100 corresponding to the predetermined amount of liquid medicine 100 to be administered to the other nasal cavity is sprayed from spraying hole 41a to the outside of syringe-shaped spraying device 1. In this way, the administration of liquid medicine 100 to the other nasal cavity is completed.

In the manner described above, all the operations are completed, thereby completing the administration of liquid medicine 100 to the pair of nasal cavities of the patient. With such a syringe-shaped spraying device 1 according to the present embodiment, it is possible to accurately administer a predetermined amount of liquid medicine 100 to each of the pair of nasal cavities of the patient while suppressing occurrence of liquid leakage during use.

In the above-described embodiment of the present invention, it has been illustratively described that the flow path for liquid medicine with a sufficiently small cross sectional area is formed inside the nozzle in such a manner that the pair of first groove portions extending in the axial direction are provided in the core accommodated inside the nozzle and the second groove portions are provided in the front end of the core. However, the flow path does not necessarily need to be thus configured. That is, the flow path may be configured in any manner as long as the flow path for liquid medicine with a sufficiently small cross sectional area is formed by the nozzle and the core with the core being accommodated inside the nozzle.

In the above-described embodiment of the present invention, it has been illustratively described that the present invention is applied to a pre-filled type syringe-shaped spraying device serving as a transnasal administration device for administering a liquid medicine to a pair of nasal cavities of a patient; however, the present invention is not limited to being applied thereto. The present invention is applicable to syringe-shaped spraying devices for other purposes of use.

The embodiments and examples disclosed herein are illustrative and non-restrictive in any respect. The scope of the present invention is defined by the terms of the claims, and is intended to include any modifications within the scope and meaning equivalent to the terms of the claims.

REFERENCE SIGNS LIST

1: syringe-shaped spraying device; 10: barrel; 11: tubular portion; 12: connecting portion; 12a: front end surface; 12b: outer circumferential surface; 12c: annular recess portion; 13: flange portion; 20: plunger; 21: rod portion; 21a: first abutment portion; 21b: second abutment portion; 22: coupler portion; 22a: external thread; 23: flange portion; 30: gasket; 31: axial hole portion; 31a: internal thread; 40: nozzle; 41: nozzle portion; 41a: spraying hole; 41b: first flow path portion; 41c: second flow path portion; 42: connected portion; 42A: first facing wall portion; 42B: second facing wall portion; 42a: first facing surface; 42b: second facing surface; 42c: first annular protrusion portion; 42d: second annular protrusion portion; 50: core; 51: large-diameter portion; 51a: first groove portion; 51b: second groove portion; 52: small-diameter portion; 60: packing; 60a: first main surface; 60b: second main surface; 61: through hole; 62a: first lip portion; 62b: second lip portion; 70: finger grip; 71: accommodation space; 72a: first insertion portion; 72b: second insertion portion; 73: stopper; 80: cap; 100: liquid medicine.

The invention claimed is:

1. A syringe-shaped spraying device comprising:
a barrel that stores a liquid;
a plunger having a front end inserted in the barrel;
a gasket attached to the front end of the plunger;
a nozzle provided with a spraying hole for spraying the liquid, the nozzle being connected to a front end of the barrel;
a packing interposed between the barrel and the nozzle, the packing having an annular shape; and
a core at least a portion of which is disposed inside the nozzle, a liquid flow path being defined between the core and the nozzle, wherein a connecting portion that connects to the nozzle is provided at the front end of the barrel, the connecting portion having a tubular shape,
the nozzle includes a first facing wall portion having an annular shape and a second facing wall portion having a tubular shape, the first facing wall portion having a first facing surface facing a front end surface of the connecting portion, the second facing wall portion having a second facing surface facing an outer circumferential surface of the connecting portion,
the packing is disposed between the front end surface of the connecting portion and the first facing surface,
the outer circumferential surface of the connecting portion is provided with an annular recess portion extending along a circumferential direction of the connecting portion,
the second facing surface is provided with a first annular protrusion portion, the first annular protrusion portion extending along a circumferential direction of the second facing wall portion, the first annular protrusion portion protruding inwardly in a radial direction of the second facing wall portion,
by engaging the first annular protrusion portion with the annular recess portion, the packing is compressed in an axial direction due to the packing being sandwiched between the front end surface of the connecting portion and the first facing surface,
the second facing surface is provided with a second annular protrusion portion at a portion located on a rear end side of the nozzle with respect to a portion of the second facing surface provided with the first annular protrusion portion, the second annular protrusion portion extending along the circumferential direction of the second facing wall portion, the second annular protrusion portion protruding inwardly in the radial direction of the second facing wall portion,
the second annular protrusion portion is in pressure contact with the outer circumferential surface of the connecting portion entirely in the circumferential direction of the connecting portion, and
the core is inserted in and extends through the packing, and is inserted in the connecting portion.

2. The syringe-shaped spraying device according to claim 1, wherein
a first lip portion having a protruding shape and extending along a circumferential direction of the packing is provided at a first main surface of the packing, the first main surface having an annular shape, the first main surface facing the first facing surface,
a second lip portion having a protruding shape and extending along the circumferential direction of the packing is provided at a second main surface of the packing, the second main surface having an annular shape, the second main surface facing the front end surface of the connecting portion, and
each of the first lip portion and the second lip portion is compressed due to the packing being sandwiched between the front end surface of the connecting portion and the first facing surface.

* * * * *